(12) United States Patent
Castro

(10) Patent No.: US 7,435,261 B1
(45) Date of Patent: Oct. 14, 2008

(54) SPINAL IMPLANT AND METHOD OF USING SPINAL IMPLANT

(76) Inventor: Frank Castro, 834 Inspiration Way, Louisville, KY (US) 40245

( * ) Notice: Subject to any disclaimer, the term of this patent is extended or adjusted under 35 U.S.C. 154(b) by 129 days.

(21) Appl. No.: 11/089,103

(22) Filed: Mar. 24, 2005

(51) Int. Cl.
*A61F 2/44* (2006.01)
(52) U.S. Cl. .................................. 623/17.11
(58) Field of Classification Search .... 623/17.11–17.16
See application file for complete search history.

(56) References Cited

U.S. PATENT DOCUMENTS

| | | | |
|---|---|---|---|
| 5,147,402 A | | 9/1992 | Bohler et al. |
| 5,425,772 A | | 6/1995 | Brantigan |
| 5,609,635 A | * | 3/1997 | Michelson ............... 623/17.16 |
| 5,766,252 A | | 6/1998 | Henry et al. |
| 6,066,175 A | | 5/2000 | Henderson et al. |
| 6,090,143 A | * | 7/2000 | Meriwether et al. ....... 623/17.11 |
| 6,117,174 A | | 9/2000 | Nolan |
| 6,159,245 A | * | 12/2000 | Meriwether et al. ....... 623/17.11 |
| 6,231,610 B1 | | 5/2001 | Geisler |
| 6,302,914 B1 | | 10/2001 | Michelson |
| 6,432,107 B1 | * | 8/2002 | Ferree ........................ 606/61 |
| 6,491,724 B1 | | 12/2002 | Ferree |
| 6,537,320 B1 | | 3/2003 | Michelson |
| 6,569,201 B2 | * | 5/2003 | Moumene et al. ......... 623/17.11 |
| 6,660,038 B2 | | 12/2003 | Bayer, II et al. |
| 6,746,484 B1 | | 6/2004 | Lin et al. |
| 6,767,367 B1 | | 7/2004 | Michelson |
| 2003/0125739 A1 | | 7/2003 | Bagga et al. |
| 2007/0016295 A1 | * | 1/2007 | Boyd ....................... 623/17.11 |

OTHER PUBLICATIONS

Barack, R. L. Revision Total Hip Arthroplasty: The Femoral Component. J. Am Acad Orthop Surg 1995; 3(2); 79-85. USA.
Castro, F.P., Jr. Stingers, Cervical Cord Neurapraxia, and Stenosis. Clin Sport Med 2003; 22: 483-492. USA.
Majd M.E, Vadhva, M., Holt R. T. Anterior Cervical Reconstruction Using Titanium Cages With Anterior Plating. Spine 1999; 24 (15): 1604-1610. USA.
Park J. B., Cho Y. S., Riew, K. D. Development of Adjacent-Level Ossification in Patient with an Anterior Cervical Plate. J. Bone Surg. 2005; 87-A; 558-563, USA.

* cited by examiner

*Primary Examiner*—Eduardo C. Robert
*Assistant Examiner*—Jerry Cumberledge
(74) *Attorney, Agent, or Firm*—Kenneth F. Pearce

(57) ABSTRACT

The present invention is a brace or spinal implant that can be inserted into vertebra that has had a cavity surgically created therein. The trapezoidal shaped spinal implant includes an opening that allows the surgical team to view the dura mater prior to packing the implant with osteogenic substances.

8 Claims, 10 Drawing Sheets

FIG 9

| Supplying a length of brace or implant that has a plurality of spaced apart trapezoidal platforms where each inward trapezoidal platform has posts that extend in opposite directions from the trapezoidal platform |
|---|

| Measuring the cavity where the implant or brace is to be inserted |
|---|

| Severing the brace or implant at one or more cross-sections to size the brace or implant to be inserted into the cavity |
|---|

| Fitting the brace or implant into the cavity such that one of the posts is generally parallel the dura mater |
|---|

| Packing the brace or implant with osteogenic material or substances |
|---|

FIG 10

| Supplying a length of brace or implant that has a plurality of spaced apart trapezoidal platforms where each inward trapezoidal platform has posts that extend in opposite directions from the trapezoidal platform |
|---|

| Measuring the cavity where the implant or brace is to be inserted |
|---|

| Severing the brace or implant at one or more cross-sections to size the brace or implant to be inserted into the cavity |
|---|

| Fitting the brace or implant into the cavity such that one of the posts is generally parallel the dura mater and at least one of the posts contacts the cavity wall |
|---|

| Packing the brace or implant with osteogenic material or substances |
|---|

SPINAL IMPLANT AND METHOD OF USING SPINAL IMPLANT

BACKGROUND OF THE INVENTION

1. Field of the Invention

Among other things, the present invention is related to a surgical brace or implant that can be inserted into a cavity that has been created by removing at least a part of one or more vertebra. The generally trapezoidal shaped brace can be supplied as a single receptacle or a span of conjoined receptacles. Each receptacle is provided with an opening that allows the surgical team to view the dura mater prior to packing the receptacle with osteogenic substances. One or more brakes can be incorporated into the spinal implant.

2. Description of the Previous Art

1) US Publish Patent Application No. 2003/0125739 Al-Bagga, et al. discloses a bioactive spinal implant and method of manufacture. Among other things, it does not appear that the Bagga invention practices the use of posts, supports or ties.

2) U.S. Pat. No. 6,767,367 B1—Michelson enables a spinal fusion implant having deployable bone engaging projections. Michelson teaches that the '367 implant 300 has a rotatable member 320 that is preferably frustoconical in shape. Rotatable member 320 has bone engaging projections 332 adapted to penetrably engage the bone of the adjacent vertebral bodies. Bone engaging projections 332 are preferably configured such that in a retracted position, implant 300 may be linearly inserted into the disc space. After implant 300 is inserted into the disc space, bone engaging projections 332 are moved to a deployed position to penetrably engage the endplates of each adjacent vertebral body and prevent the expulsion of implant 300 from the disc space.

3) U.S. Pat. No. 6,537,320 B1—Michelson enables a self-broaching, rotable, push-in interbody spinal fusion implant and method for its deployment. Among other things, it does not appear that the Michelson invention practices the use of posts, supports or ties.

4) U.S. Pat. No. 5,609,635—Michelson enables a lordotic interbody spinal fusion implant. The Michelson Summary of the Invention teaches that the '635 modular implants are generally wedge-shaped that have upper and lower surfaces conforming to the contours of the vertebral endplates, which contours include but are not limited to being relatively flat or convex. Michelson states, "As the disc spaces in the lumbar spine are generally lordotic, said implants in the preferred embodiment would be taller anteriorly, that is at the implant's insertion end, and less tall posteriorly, that is at the implant's trailing end. To introduce an implant that is taller at its insertion end than the space available at the posterior aspect of the disc space, even when that disc space is optimally distracted, is problematic."

5) U.S. Pat. No. 6,302,914 B1—Michelson enables a lordotic interbody spinal fusion implant. The '914 patent is a continuation patent of the U.S. Pat. No. 5,609,635—Michelson patent.

6) U.S. Pat. No. 6,066,175—Henderson, et al. enables a fusion stabilization chamber. Mesh cage 41 sits between vertebral bodies 43 and 45. Intervertebral discs 46 and 47 flank the vertebral bodies. The spinal cord is indicated by reference numeral 53. Cage 41 fills the space previously occupied by another such disc. The cage includes barrel vaults 48 and 49, and has flanges 50 and 51 which help to anchor the cage on the vertebral bodies and provide means for attachment thereto. The Henderson flanges also prevent the cage from being inadvertently tapped into the spinal cord, and they also distribute the shear and bending moment and thus increase the stability of the device. The flanges also provide one or more additional holes to accommodate more screws for affixing the device to the vertebral bodies. Both the flanges and barrel vaults are preferably integral with the cage. The barrel vaults can be either threaded or non-threaded. The screws which are inserted through the barrel vaults are preferably of the locking type, so that they lock into the barrel vaults when fully inserted. The cage is preferably rectangular when viewed from the top or the bottom. The cage may be constructed such that the bottom (the side pointed towards the spinal cord) is solid and not made of mesh. The top of the cage could also be solid. A mesh structure is most necessary on the sides of the cage, where the cage abuts the vertebral bodies, so as to promote fusion between the bone chips or bone substitute material inside the cage and the adjacent vertebral bodies.

7) U.S. Pat. No. 5,766,252—Henry, et al. enables an interbody spinal prosthetic implant and method. Among other things, the Henry device practices threaded hole 38 and longitudinal struts 84.

8) U.S. Pat. No. 5,425,772—Brantigan enables a prosthetic implant for intervertibral spinal fusion. Among other things, the '772 device practices traverse teeth or serrations 19 where the teeth have sharp peaks 19a, slopping walls 19b and valleys 19c.

9) U.S. Pat. No. 5,147,402—Bohler, et al. enables an implant for ingrowth of osseous tissue. Among other things, Bohler does not appear to practice a generally wedge shaped cage.

10) U.S. Pat. No. 6,746,484—Liu, et al. enables a spinal implant. Among other things, the Liu disclosure teaches that tool 22 has a milling cutter 23, central cutting portion 24 and two non-cutting portions 31, 36 arranged at opposite ends of central cutting portion 24. Non-cutting portions 31, 36 have height h corresponding to the intersomatic space and permitting uniform, symmetrical cutting of a predetermined length through a central region of both vertebral plates 15, 16. The geometry of portions 24, 31, 36 is determined for preparing the intersomatic space with the geometry of implant 1 to restore the natural lordosis of the intervertebral space, and correspondingly the distances represented by h and d1 are approximately equal.

11) U.S. Pat. No. 6,231,610 B1—Geisler enables an anterior cervical column support device. The '610 apparatus utilizes serrations on the load bearing surfaces and two screw holes.

12) U.S. Pat. No. 6,660,038 B2—Boyer, et al. enables skeletal reconstruction cages. The Boyer patent discloses an end cap 210 suitable for coupling to central shaft 160 includes an outer wall 212, as well as a central hole disposed along axis 213 with a lower inner wall 214, an upper inner wall 216, and an inner ridge portion 218. Lower inner wall 214 extends about a depth H2 and is sized to fit snugly on an upper or lower portion 182, 184 of central shaft 160 with an upper or lower face 162, 164 abutting a shoulder 218. Preferably, upper inner wall 216 has a dimension that is about the same as dimension Ds of hole 178 of central shaft 160. End cap 210 is symmetrical about line 220, and is generally oblong in shape with first and second widths $W_2$, $W_3$. Notably, while outer wall 176 of central shaft 160 is generally circular, outer wall 212 of end cap 210 is generally oblong, so that a generally I-shaped skeletal reconstruction cage may be formed when a pair of end caps 210 are placed on central shaft 160.

13) U.S. Pat. No. 6,491,724—Ferree enables a spinal fusion cage with lordosis correction. Among other things, the '724 patent teaches, "In the preferred embodiment, the anterior portion 112 includes mating members 120 and 122 with teeth 124 or other features to form a locking or ratchet mechanism, as shown. Whatever apparatus is used, the purpose is to maintain the height of the anterior portion of the cage at a desired level consistent with lordosis upon installation."

14) U.S. Pat. No. 6,117,174—Nolan enables a spinal implant device. Among other things, the '174 apparatus utilizes disc 14 made of the same material as body 12. Inner surfaces of legs 18 and 20 are curved.

SUMMARY OF THE INVENTION

Unlike traditional spinal implants, the present invention provides a spinal implant that can be packed with bone graft and/or other osteogenic materials or substances after the spinal implant has been inserted into a surgically created cavity of one or more vertebra. Prior to packing the receptacle with osteogenic substances, the surgical team can view the dura mater of the spinal cord. When inserting the brace, during a surgical procedure, the wedge-like shape of the implant assists the surgical team in not impinging the spinal cord with the brace. Post operative and prior to complete arthrodesis, the generally wedge-like shape of the implant inhibits extrusion of the brace against the spinal cord.

An aspect of the present invention is to provide a generally wedge-shaped spinal surgical implant or brace.

Still another aspect of the present invention is to provide a spinal implant having a trapezoidal shaped platform or divider.

It is another aspect of the present invention to enable a method of implanting the generally trapezoidal shaped brace into a surgically created cavity of one or more vertebra.

Yet another aspect of the present invention is to provide a receptacle of an implant that after insertion into the surgically created cavity allows the surgical team to view the dura mater of the spinal cord through an opening of the receptacle.

Still another aspect of the present invention is to provide a receptacle of an implant that allows the packing of bone graft and/or osteogenic materials or substances through an opening facing the surgical team after the receptacle is inserted into the surgically created cavity.

It is still another aspect of the present invention to provide an implant having select embodiments that can be implanted through the patient's frontal side.

Yet still another aspect of the present invention is to provide a brace that includes a span of conjoined receptacles.

It is still another aspect of the present invention to provide an implant that includes a span of consecutively joined receptacles, where the span can be severed across a first cross-section or a first cross-section and a second cross-section to create a custom fitted implant for the surgically created cavity.

Still another aspect of the present invention is to provide an implant having a plurality of apertures.

An embodiment of the present invention can be described as a brace for insertion into a cavity created by surgical removal of a part of one or more vertebra of a spinal column; said brace comprising: a first trapezoidal platform having an aperture therein comprising: a first brake, a first converging side, a second converging side, a shorter side; a second trapezoidal platform having an aperture therein comprising: a second brake, a first converging side, a second converging side, a shorter side; a first corner post extending between a first converging corner of the first trapezoidal platform and a corresponding first converging corner of the second trapezoidal platform; a second corner post extending between a second converging corner of the first trapezoidal platform and a corresponding second converging corner of the second trapezoidal platform; a first post extending between the first converging side of the first trapezoidal platform and the first converging side of the second trapezoidal platform; a second post extending between the second converging side of the first trapezoidal platform and the second converging side of the second trapezoidal platform; and a frontal post intermediate between the first corner Another embodiment of the present apparatus can be described as a brace for insertion into a cavity created by surgical removal of a part of one or more vertebra of a spinal column; said brace comprising: a trapezoidal platform having an aperture therein comprising: a first brake, a first converging side, a second converging side, a shorter side; a first corner spike extending from a first converging corner of the trapezoidal platform; a second corner spike; a third spike; and a fourth spike.

Yet another embodiment of the present invention and method can be described as a method of inserting a custom fitted brace into a cavity created by surgical removal of a part of one or more vertebra of a spinal column, comprising the steps of: supplying a length of said brace for a surgical procedure, wherein the brace further comprises: a plurality of spaced apart trapezoidal platforms, wherein each inward trapezoidal platform further comprises: first corner posts connected to the platform and extending in opposite directions from the platform, second corner posts connected to the platform and extending in opposite directions from the platform, third posts connected to the platform and extending in opposite directions from a first side of the platform, and fourth posts connected to the platform and extending in opposite directions from a second side of the platform; measuring the cavity; sizing the by severing the brace at one or more cross-sections; fitting the brace into said cavity; and packing said brace with osteogenic material.

In still another embodiment, the present invention can be described as an implant for insertion into a cavity created by surgical removal of a part of one or more vertebra of a spinal column comprising: a span of consecutively joined receptacles for receiving packing of osteogenic materials, wherein each receptacle includes an opening for receiving packing of osteogenic materials after implantation of the implant, and wherein each consecutively joined receptacle further comprises: a generally trapezoidal shaped divider; first corner supports connected to the divider and extending in opposite directions from the divider; second corner supports connected to the divider and extending in opposite directions from the divider; third supports connected to the divider and extending in opposite directions from a first lateral side of the divider; and fourth supports connected to the divider and extending in opposite directions from a second lateral side of the divider.

Yet another embodiment of the present device can be described as an implant for insertion into a cavity created by surgical removal of a part of one or more vertebra of a spinal column comprising: a first generally trapezoidal shaped platform; a first corner support extending from the generally trapezoidal shaped platform; a second corner support extending from the generally trapezoidal shaped platform in a direction congruous to the first corner support; a third support extending from a first converging side of the generally trapezoidal shaped platform in a direction generally congruous the first corner support; and a fourth support extending from a second converging side of the generally trapezoidal shaped platform in a direction generally congruous the second corner support.

It is the novel and unique interaction of these simple elements which creates the apparatus and methods, within the ambit of the present invention. Pursuant to Title 35 of the United States Code, descriptions of preferred embodiments follow. However, it is to be understood that the best mode descriptions do not limit the scope of the present invention.

BRIEF DESCRIPTION OF THE DRAWINGS

FIG. 9 is an exemplification of the steps of an embodiment of the current method.

FIG. 10 is a diagrammatic representation of the steps of another embodiment of the present invention.

DESCRIPTION OF THE PREFERRED EMBODIMENTS

Figure 1:
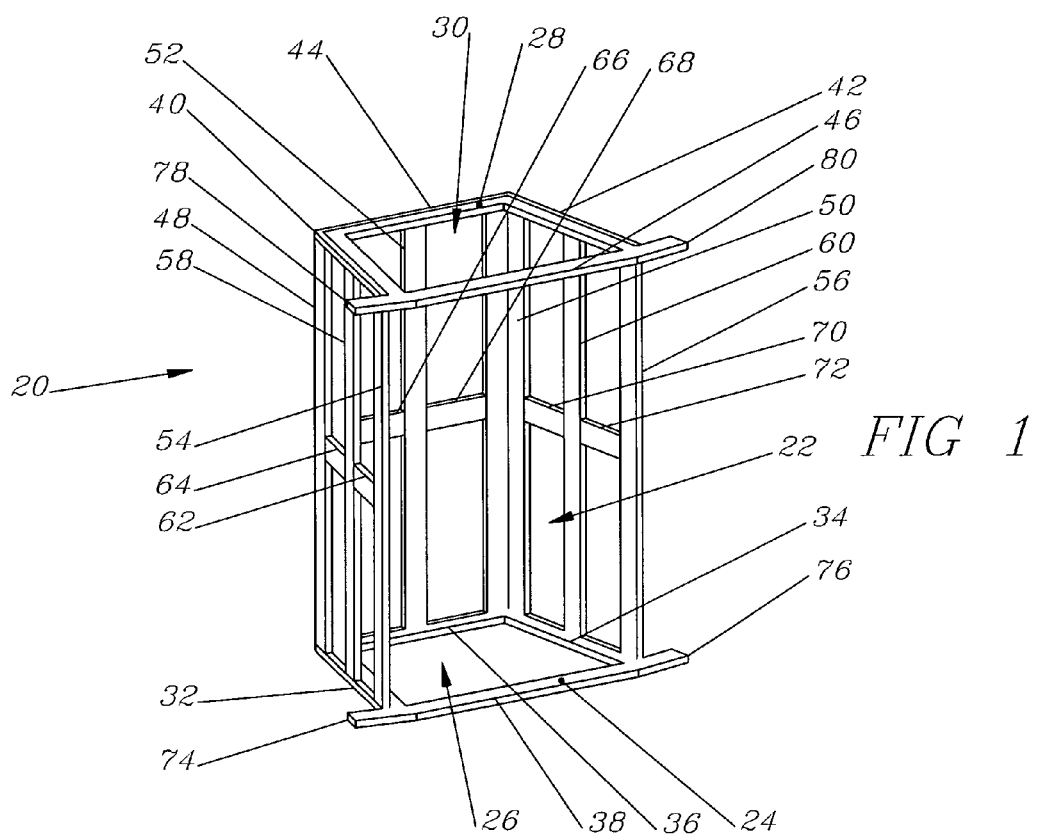
FIG. 1 is a frontal perspective of an embodiment of a receptacle of the present invention.

Although the disclosure hereof is detailed to enable those skilled in the art to practice the invention, the embodiments published herein merely exemplify the present invention.

In the most general sense, the present invention is a brace or implant that can be inserted into a cavity of the spinal column. Surgical removal of at least a part of one or more vertebra creates the cavity that will receive the implant. It has been discovered that many embodiments of the current implant can be useful for cervical spine surgeries and can assist in stabilization of the postoperative spine. And many of the preferred embodiments of the present invention are particularly suited for corpectomy or partial corpectomy procedures.

After insertion of the brace into the cavity, the brace assists in stabilizing the spinal column against rotational movement and also resists the compression forces associated with gravitational forces on the spinal column. Select embodiments of the present invention can be implanted through the patient's frontal side, e.g., the frontal side of the patient's neck. Depending on the required surgical parameters, such as the length of the cavity and the number of vertebra involved in the procedure, the brace or implant can include a span of receptacles for receiving bone graft and/or other osteogenic substances. When a conjoined receptacle embodiment is practiced, the implant can be custom fitted to the desired size for the cavity into which the implant will be inserted. In one embodiment, the custom fitted implant can be created by severing through a cross-section of the brace, thereby creating two sections of the implant, including the one that is to be inserted into the cavity. In other embodiments, the custom fitted implant can be created by severing through a first cross-section and a second cross-section of the brace.

Preferred embodiments of the current spinal implant are generally trapezoidal in shape and are manufactured of titanium alloys, stainless steel, resorbable polymers or any other composition acceptable in the art. Within the scope of the present invention, it has advantageously been discovered that receptacles can have a height of approximately twelve millimeters, a width of from about six to about fifteen millimeters as measured along the narrowest parallel of the trapezoid and a depth of from about eight millimeters to about fifteen millimeters as measured along a converging side of the trapezoid. The size of implant to be inserted in the cavity is dependent upon the volume of the cavity. Prior to the surgical procedure, spans of braces of differing sizes can be provided to the surgical team—allowing the surgical team to select the appropriate volume and length for the implant to be inserted into the surgically created cavity. After a brace or implant has been inserted into the cavity, openings of the receptacles into which bone graft, osteogenic and/or arthrodesis accelerating substances are packed can have areas from about 36 millimeters to 225 millimeters$^2$ or greater.

Each receptacle of the present invention can be provided with corner posts or supports and other posts or supports that extend the height of the receptacle. Posts and corner posts are spaced about the outer border of the receptacle. One or more ties can extend crosswise between the posts and corner posts. Corner supports and the other supports are from about one millimeter to about two millimeters wide and are situated along the outer periphery of the receptacle in such a way as to create apertures between the posts and corner posts. Depending on the volume of the implant, the apertures between the corner posts and the other posts are from about one millimeter to about two millimeters wide.

Meeting a long felt but unfilled need in the spinal surgical arts, the unique structures of the present invention allow the surgical team to view the dura mater, before a receptacle is packed with bone graft, osteogenic and/or arthrodesis accelerating substances. Allowing the surgical team to view the dura mater while inserting the implant into the cavity reduces the possibility of having the brace inadvertently contact or injure the spinal cord. At the same time, the generally trapezoidally-shaped brace also assists the surgical team in not inserting the implant against the spinal cord. The contact between the cavity wall and the wedge-like brace can inhibit the implant from contacting the spinal cord. It appears that having the apertures of select embodiments in such close proximity with the cavity's walls increases the probability of the osteogenic materials procuring a blood supply. And it is believed that increasing the blood supply to the osteogenic materials held by a receptacle enhances local areas of arthrodesis between the vertebra and the bone graft. Select preferred embodiments of the present invention are also provided with brakes to further impede the implant from contacting the spinal column.

FIG. 1 is a frontal perspective of an embodiment of a receptacle of the present invention. When implanted into a surgically created cavity of the spinal column, opening (22) of receptacle or brace (20) will face the surgical team. A first trapezoidal platform (24) includes aperture (26) and a second trapezoidal platform (28) includes aperture (30). First platform (24) includes first converging side (32), second converging side (34), shorter side (36) and longer side (38). Second platform (28) is provided with first converging side (40), second converging side (42), shorter side (44) and longer side (46). Platform (24) is spaced apart from platform (28), and corner posts (48) and (50) extend between first platform (24) and second platform (28). Intermediate of first corner post (48) and second corner post (50) is frontal post (52). Proximate longer side (38) of platform (24) and longer side (46) of platform (28) and extending between platform (24) and platform (28) are posts (54) and (56).

Although not required to practice the present invention, as shown in FIG. 1, in select preferred embodiments, positioned between corner post or support (48) and post or support (54) is post or support (58) that extends between first converging side (32) of platform (24) and first converging side of (40) of platform (28). In a similar manner, post or support (60) is positioned between corner post or support (50) and post or support (56) and extends between second converging side (34) of platform (24) and second converging side of (42) of platform (28). Select preferred embodiments can include one or more ties extending between or connecting the posts or supports.

By way of illustration, as shown in FIG. 1, tie (62) connects post (54) and post (58), tie (64) connects post (58) and post (48), tie (66) connects post (48) and post (52), tie (68) connects post (52) and post (50), tie (70) connects post (50) and post (60) and tie (72) connects post (60) and post (56). When surgical parameters mandate, one or more ties can be eliminated from brace (20). In an alternate preferred embodiment, a first tie can connect all posts positioned along the first converging side (32, 40) of implant (20), a second tie can connect all posts located near the frontal plane of brace (20) and a third tie can connect all posts positioned along the second converging side (34, 42) of receptacle (20).

When surgical parameters dictate, more than three or less than three posts can be positioned along either the first converging side, the second converging side or both of implant (20). In an alternate preferred embodiment, frontal post (52) can be eliminated. And in select preferred embodiments, instead of a plurality of ties interconnecting with the various posts, a single tie can interconnect posts (48), (50), (52), (54), (56), (58) and (60).

With reference still to FIG. 1, brake (74) extends laterally of first converging side of platform (24) and brake (76) extends laterally of second converging side of platform (24). Brake (78) extends laterally of first converging side of platform (28) and brake (80) extends laterally of second converging side of platform (28). Depending upon preselected parameters, for an embodiment employing brakes, a receptacle can be provided with one or more brakes.

Figure 2:
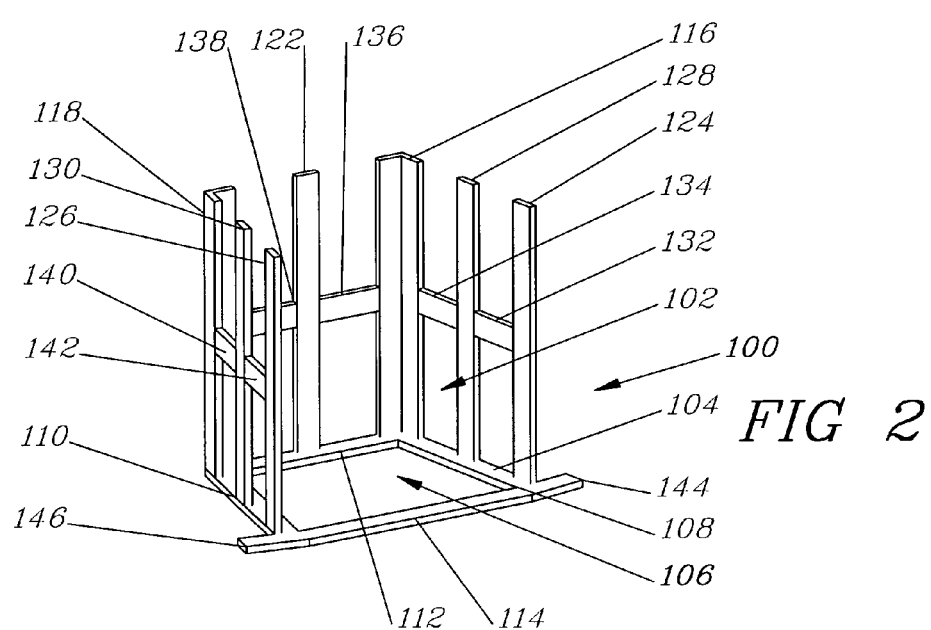
FIG. 2 is a frontal perspective of another embodiment of a receptacle of the present invention.

FIG. 2 is a frontal perspective of another embodiment of a receptacle of the present invention. When implanted into a surgically created cavity of the spinal column, opening (102) of receptacle or brace (100) will face the surgical team. Trapezoidal platform (104) includes aperture (106), first converging side (108), second converging side (110), shorter side (112) and longer side (114). First corner spike (116) and second corner spike (118) extend from shorter side (112) of platform (104). Seventh spike (122) is intermediate first corner spike (116) and second corner spike (118). Third spike (124) and fifth spike (128) extend from first converging side (108). Fourth spike (126) and sixth spike (130) extend from second converging side (110) of platform (104). As shown in FIG. 2, seven spikes are strategically extended from platform (104). However, when surgical parameters mandate, more or less than seven spikes can be extended from platform (104).

Select preferred embodiments can include one or more ties extending between or connecting the spikes. By way of illustration, as shown in FIG. 2, tie (132) connects spike (124) and spike (128), tie (134) connects spike (128) and spike (116), tie (136) connects spike (116) and spike (122), tie (138) connects spike (122) and spike (118), tie (140) connects spike (118) and spike (130) and tie (142) connects spike (130) and spike (126). When surgical parameters mandate, one or more ties can be eliminated from brace (100). In an alternate preferred embodiment, a first tie can connect all spikes positioned along the first converging side (108) of implant (100), a second tie can connect all spikes extending from shorter side (112) of brace (100) and a third tie can connect all spikes positioned along the second converging side (110) of receptacle (100). In select preferred embodiments, instead of a plurality of ties interconnecting with the various spikes, a single tie can interconnect spikes (116), (118), (122), (124), (126), (128) and (130). Brake (144) extends laterally of first converging side (108) of platform (104) and brake (146) extends laterally of second converging side (110) of platform (104).

Figure 3:
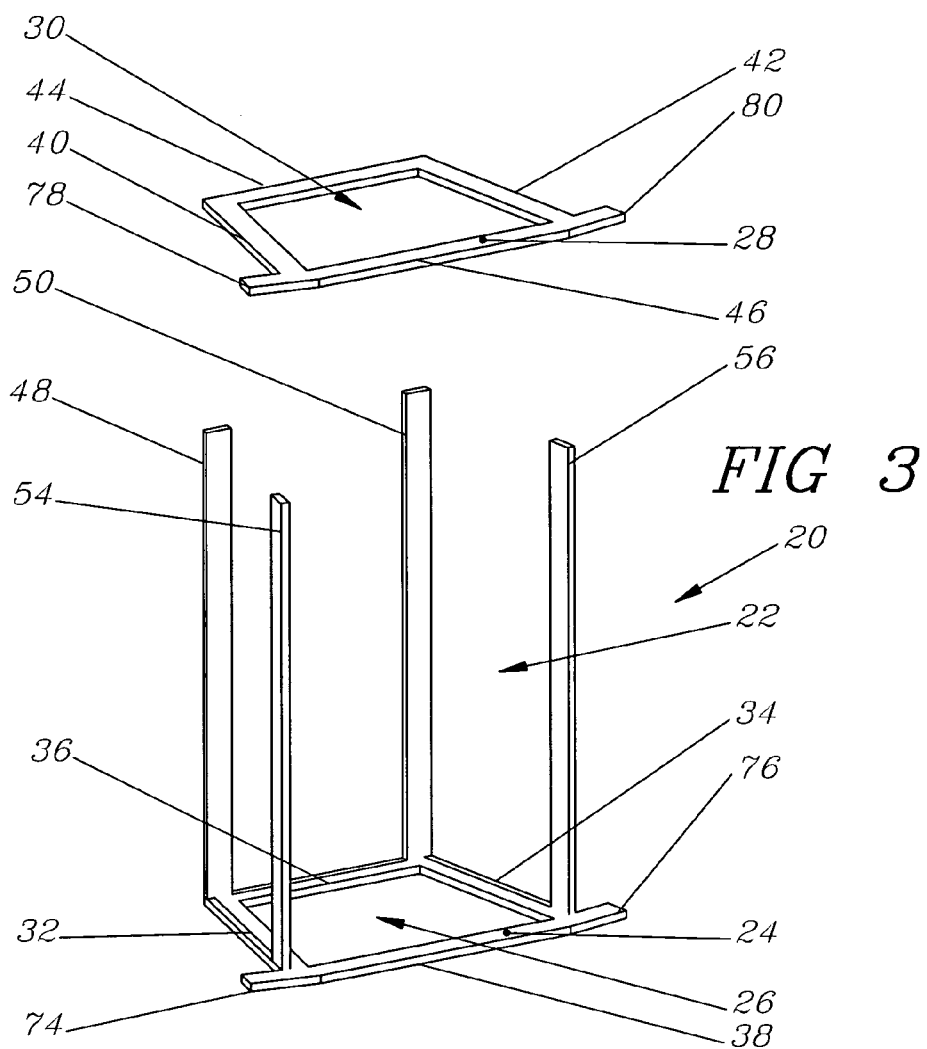
FIG. 3 is an exploded view of another embodiment of the present invention that does not utilize ties.

FIG. 3 is an exploded view of another embodiment of the present invention. When implanted into a surgically created cavity of the spinal column, opening (22) of receptacle or brace (20) will face the surgical team. A first trapezoidal platform (24) includes aperture (26) and a second trapezoidal platform (28) includes aperture (30). First platform (24) includes first converging side (32), second converging side (34), shorter side (36) and longer side (38). Second platform (28) is provided with first converging side (40), second converging side (42), shorter side (44) and longer side (46). When connected to receptacle (20), platform (28) is spaced apart from platform (24). Corner supports or posts (48) and (50) extend from first platform (24). Positioned proximate longer side (38) and extending from platform (24) are support (54) and support (56). Although not shown in FIG. 3, select preferred embodiments can include one or more ties extending between or connecting the supports. Brakes (74), (76), (78) and (80) extend laterally from the converging sides of platforms (24) and (28).

Figure 4:
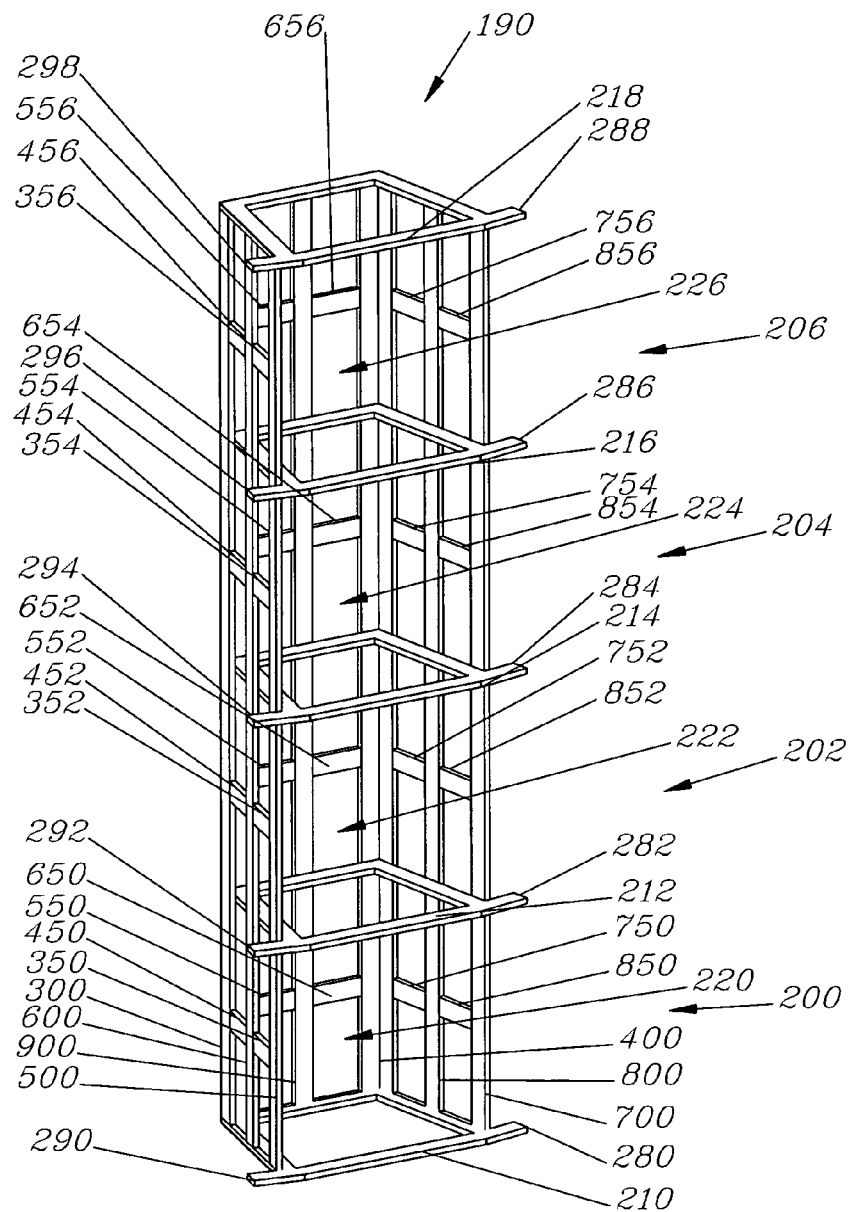
FIG. 4 is a frontal view of a span of consecutively joined receptacles.

FIG. 4 is a frontal view of span (190) of consecutively joined receptacles. As shown, by way of illustration rather than limitation, as to the number of receptacles, supports, ties or brakes, span (190) includes receptacles (200), (202), (204) and (206). Receptacle (200) includes dividers (210) and (212); receptacle (202) includes dividers (212) and (214); receptacle (204) includes dividers (214) and (216); and receptacle (206) includes dividers (216) and (218). Each divider (210, 212, 214, 216, 218) is provided with a shorter side, a longer side, a first converging side and a second converging side. Receptacles (200, 202, 204 and 206) have openings (220, 222, 224 and 226), respectively. The openings allow the surgical team to view the dura mater before one or more receptacles is packed with osteogenic substances or materials.

Receptacles (200) and (206) are end receptacles of span (190). Receptacles (202) and (204) are conjoined receptacles of span (190). Corner support (300) extends between divider (210) and divider (218) and corner support (400) extends between divider (210) and divider (218). First converging side of span (190) includes first support (500) and second support (600) extending between divider (210) and divider (218) second converging side of span (190) includes third support (700) and fourth support (800) extending between divider (210) and divider (218). Intermediate support (900) extends between divider (210) and divider (218).

With reference to receptacle (200), tie (350) connects first support (500) and second support (600); tie (450) connects second support (600) and corner support (300); tie (550) connects corner support (300) and intermediate support (900); tie (650) connects intermediate support (900) and corner support (400); tie (750) connects corner support (400) and fourth support (800); and tie (850) connects fourth support (800) and third support (700). With reference to receptacle (202), tie (352) connects first support (500) and second support (600); tie (452) connects second support (600) and corner support (300); tie (552) connects corner support (300) and intermediate support (900); tie (652) connects intermediate support (900) and corner support (400); tie (752) connects corner support (400) and fourth support (800); and tie (852) connects fourth support (800) and third support (700). With reference to receptacle (204), tie (354) connects first support (500) and second support (600); tie (454) connects second support (600) and corner support (300); tie (554) connects corner support (300) and intermediate support (900); tie (654) connects intermediate support (900) and corner support (400); tie (754) connects corner support (400) and fourth support (800); and tie (854) connects fourth support (800) and third support (700). With reference to receptacle (206), tie (356) connects first support (500) and second support (600); tie (456) connects second support (600) and corner support (300); tie (556) connects corner support (300) and intermediate support (900); tie (656) connects intermediate support (900) and corner support (400); tie (756) connects corner support (400) and fourth support (800); and tie (856) connects fourth support (800) and third support (700).

Divider (210) is provided with brakes (280) and (290); divider (212) is provided with brakes (282) and (292); divider (214) is provided with brakes (284) and (294); divider (216) is provided with brakes (286) and (296); and divider (218) is provided with brakes (288) and (298). As shown in the FIG. 4 embodiment, dividers (210 and 218) adjoin supports (300, 400, 500, 600, 700, 800 and 900), whereas dividers (212, 214 and 216) are positioned inwardly from supports (300, 400, 500, 600, 700, 800 and 900). However, depending on engineering parameters, other embodiments can include spans where each divider is flush with the supports, spans where each divider is positioned inwardly from the supports or spans where the supports are positioned inwardly from the dividers.

Figure 5:
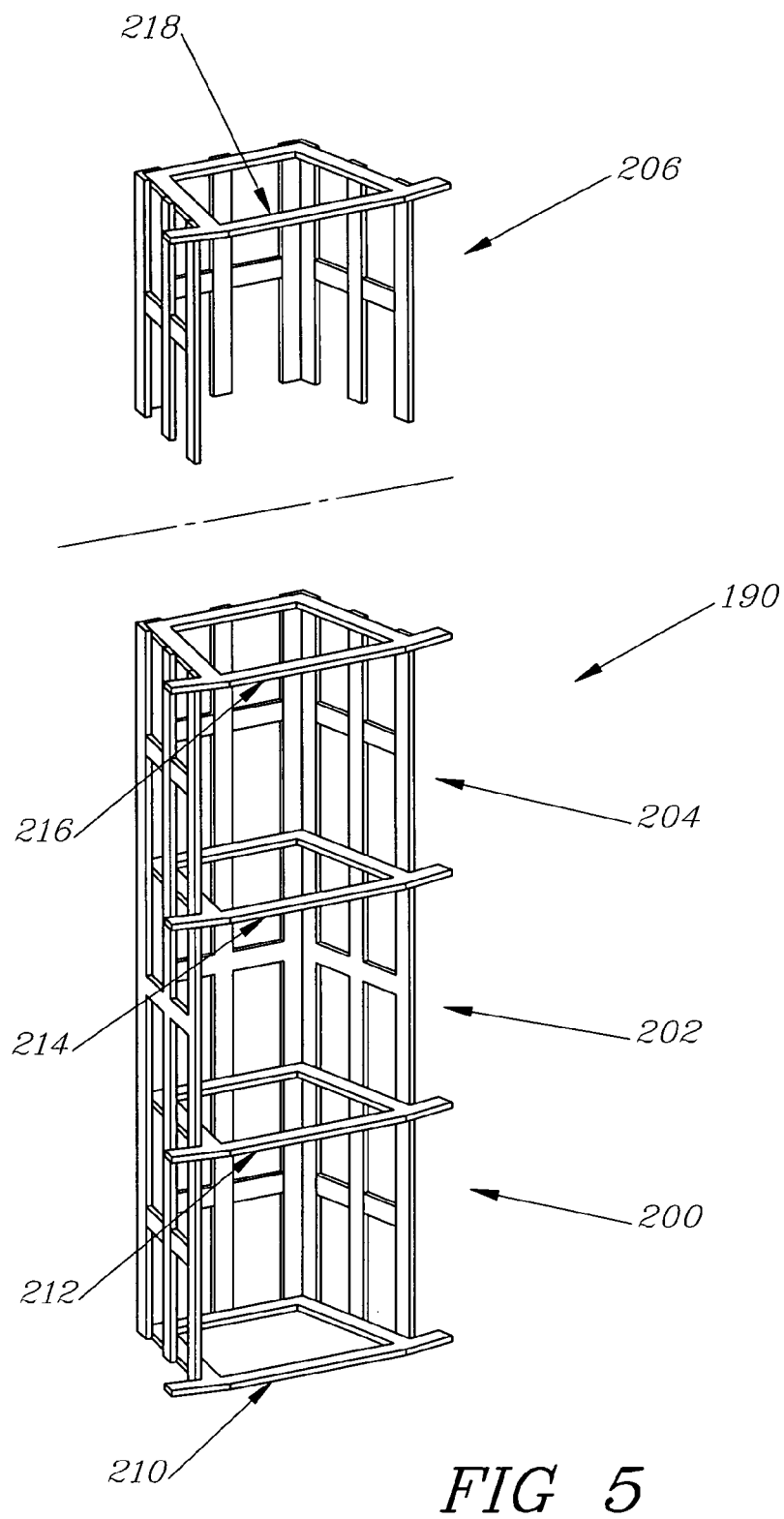
FIG. 5 is an exploded view of the invention of FIG. 4 where span (190) has been severed along a first cross-section to separate receptacle (206) away from span (190)—leaving an implant with a generally trapezoidal shaped platform or divider (210) at a first end of the implant and a generally trapezoidal shaped platform or divider (216) at a second end of the implant.

FIG. 5 is an exploded view of span (190) that has been severed along a first cross-section to separate receptacle (206) away from the remainder of span (190) and receptacles (200, 202 and 204)—leaving an implant with a generally trapezoidal shaped platform or divider (210) at a first end of the implant and a generally trapezoidal shaped platform or divider (216) at a second end of the implant. As shown in FIG. 5, each divider is positioned inwardly of the supports.

Figure 6:
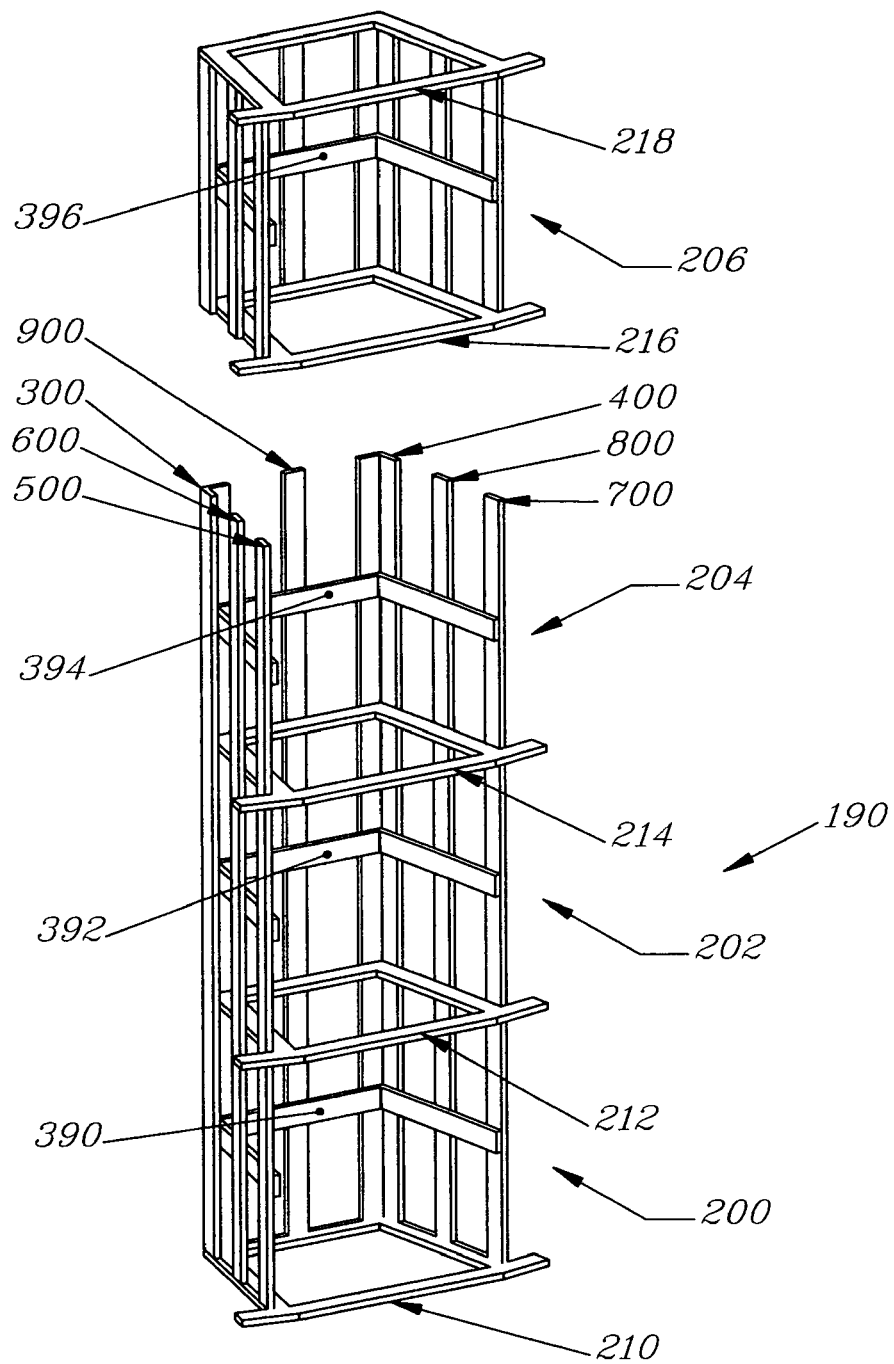
FIG. 6 is an exploded view of the invention of FIG. 4 where span (190) has been severed along a first cross-section to create an implant with a generally trapezoidal shaped divider (210) at a first end of the implant and supports or spikes (304, 404, 504, 604, 704, 804 and 904) exposed at the opposite and second end of span (190).

FIG. 6 is an exploded view of the an embodiment similar to the invention of FIG. 4. Rather than a plurality of ties for receptacles (200), (202), (204) and (206), a single tie is incorporated into each receptacle. Tie (390) reinforces receptacle (200); tie (392) reinforces receptacle (202); tie (394) reinforces receptacle (204) and tie (396) reinforces receptacle (206). As shown in FIG. 6, span (190) has been severed along a first cross-section to create an implant with a generally trapezoidal shaped divider (210) at a first end of the implant and supports or spikes (300, 400, 500, 600, 700, 800 and 900) exposed at the opposite and second end of span (190).

Figure 7:
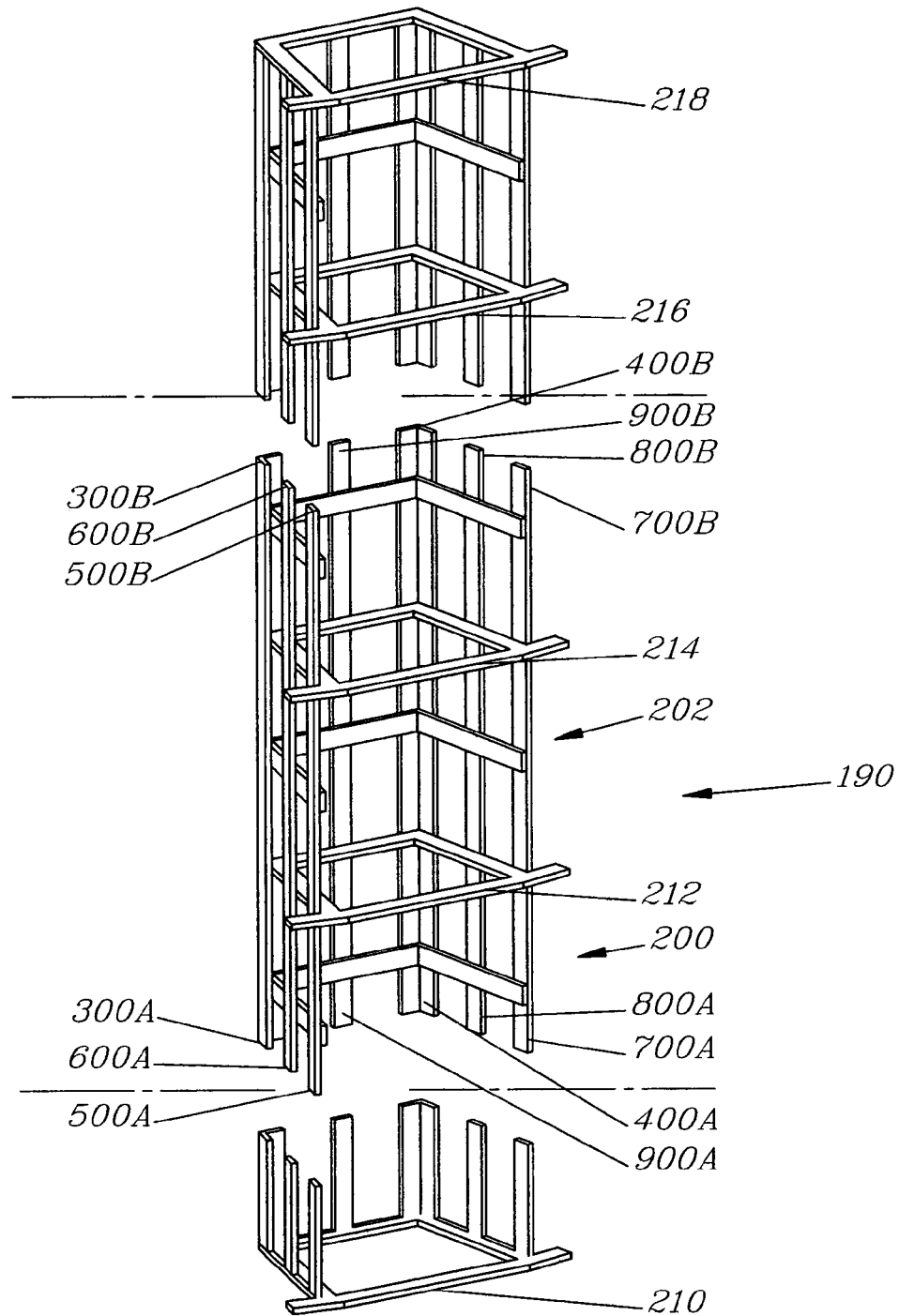
FIG. 7 is an exploded view of the invention of FIG. 4 where span (190) has been severed along a first cross-section and a second cross-section to create an implant with supports or spikes (300, 400, 500, 600, 700, 800 and 900) at first end of the implant and supports or spikes (304, 404, 504, 604, 704, 804 and 904) exposed at the opposite and second end of span (190).

FIG. 7 is an exploded view of the invention of FIG. 6 where span (190) has been severed along a first cross-section and a second cross-section to create an implant with supports or spikes (300A, 400A, 500A, 600A, 700A, 800A and 900A) at first end of the implant and supports or spikes (300B, 400B, 500B, 600B, 700B, 800B and 900B) exposed at the opposite and second end of span (190).

Figure 8:
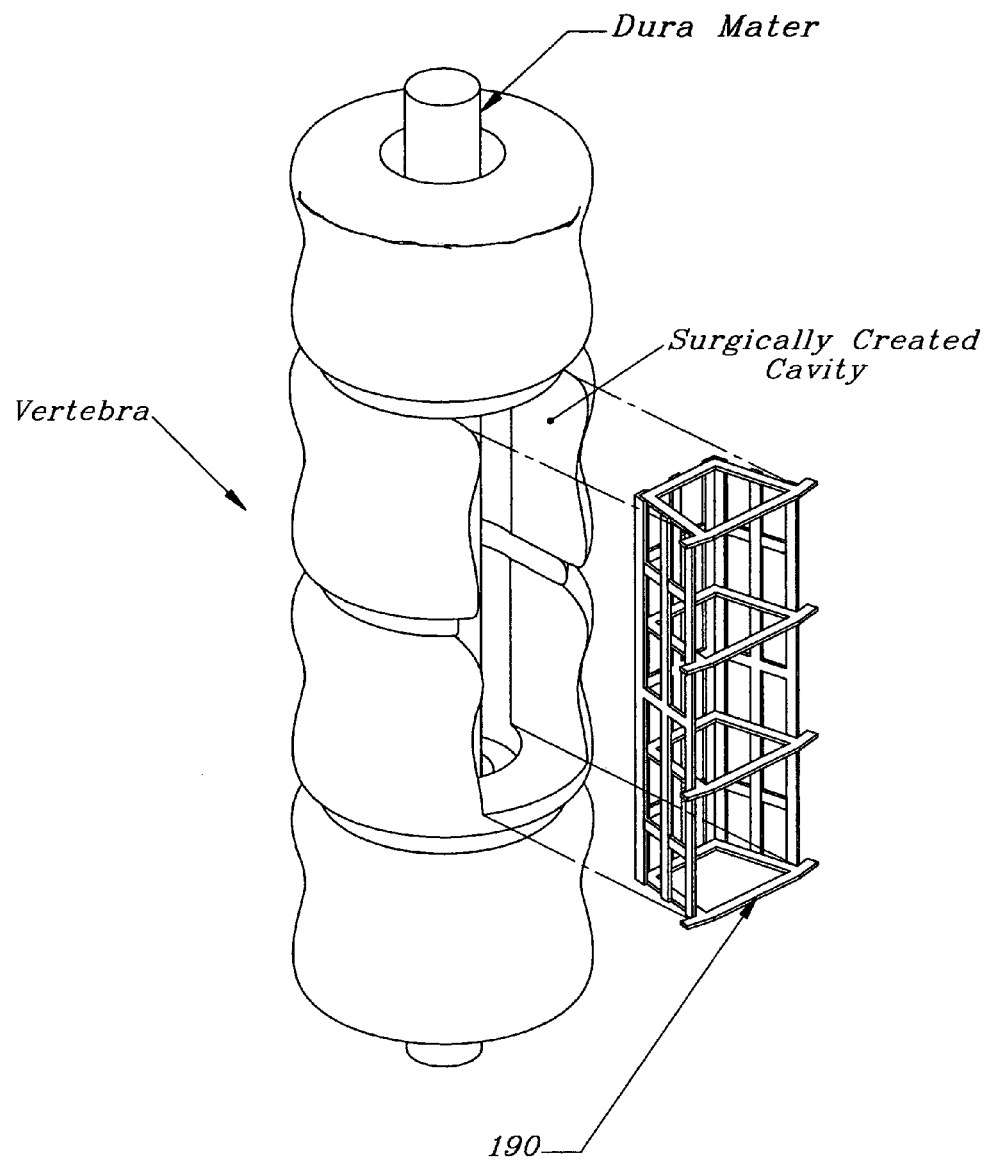
FIG. 8 is a perspective of a surgically created cavity in a vertebra and an embodiment of the present invention.
Figure 11:
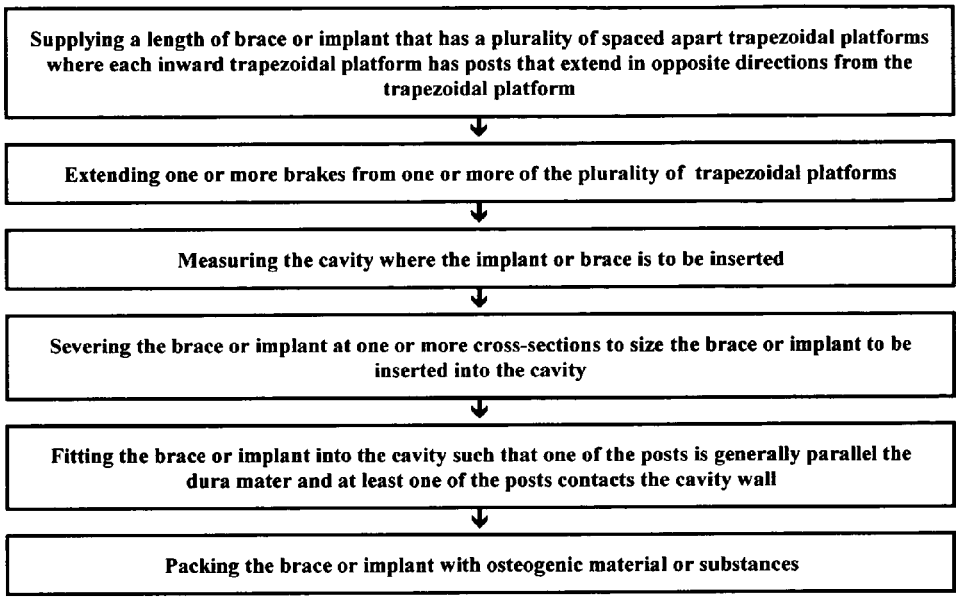
FIG. 11 is another diagrammatic representation of the steps of still another embodiment of the present invention.
Figure 12:
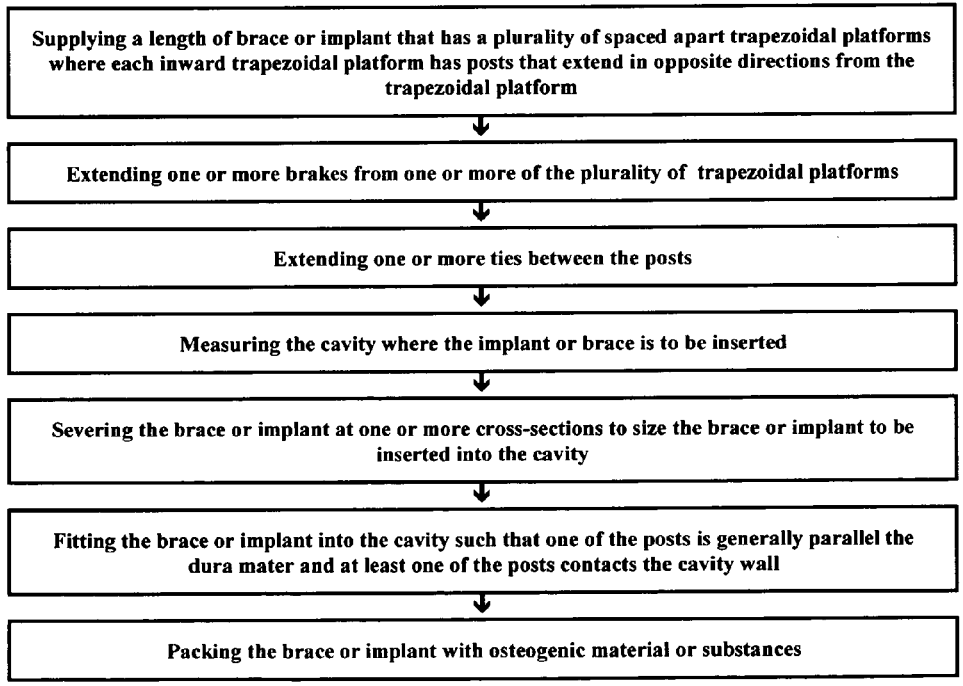
FIG. 12 is yet another exemplification of the steps of yet another embodiment of the present invention.

FIG. 8 portrays an embodiment of a span (190) of the present invention that can be inserted into a surgically created cavity of a vertebra.

Steps associated with the practice of the methods of embodiments the present invention are set forth in FIGS. 9-12. Those steps are related to the practice of using the spinal implant structures previously set forth. Moreover, the majority of the preferred embodiments of the present invention practice the packing of osteogenic materials or substances into the implant's receptacle after the brace has been inserted into the cavity. Importantly, preferred methods of the current invention can be used to create implants that have a trapezoidal platform at each end of the implant, a trapezoidal platform at the first end of the brace and a set of spikes corresponding to the posts at the second end of the implant or a set of spikes at each end of the implant.

Having disclosed the invention as required by Title 35 of the United States Code, Applicant now prays respectfully that Letters Patent be granted for his invention in accordance with the scope of the claims appended hereto.

What is claimed is:

1. A custom fitted implant, comprising a material from the group consisting of titanium alloys, stainless steel or resorbable polymers, for use in a corpectomy surgical procedure and implantation into a surgically created corpectomy cavity such that said custom fitted implant extends along a vertical axis between a superior side and an inferior side of said corpectomy cavity; said custom fitted implant, comprising: a vertical span of consecutively joined receptacles into which osteogenic substances are packed before completion of said corpectomy surgical procedure, and wherein each consecutively joined receptacle further comprises:

a) a first generally trapezoidal shaped divider;
   b) a first support connected to said first generally trapezoidal shaped divider and extending in opposite directions from said first generally trapezoidal shaped divider, wherein said first corner support is angled at about ninety degrees to simultaneously connect with a first lateral side and a short side of said trapezoidal shaped divider;
   c) a second support connected to said first generally trapezoidal shaped divider and extending in opposite directions from said first generally trapezoidal shaped divider, wherein said second corner support is angled at about ninety degrees to simultaneously connect with a second lateral side opposite said first lateral side and said short side of said trapezoidal shaped divider;
   d) a first set of superior and inferior apertures between said first set of corner supports and said second set of corner supports, such that, prior to addition of osteogenic substances to said custom fitted implant, a surgeon can see through said first set of superior and inferior apertures;
   e) a third support connected to said first generally trapezoidal shaped divider, extending in opposite directions from said first lateral side of said first generally trapezoidal shaped divider and distal from said first corner support;
   f) a fourth support connected to said first generally trapezoidal shaped divider, extending in opposite directions from said second lateral side of said first generally trapezoidal shaped divider and distal from said second corner support;

g) a first brake attached to a first long side of said trapezoidal shaped divider, wherein said first brake extends laterally outward from said first lateral side of said trapezoidal shaped divider; and h) a second set of superior and inferior apertures between said third and said fourth supports, such that, prior to addition of osteogenic substances to said custom fitted implant, a surgeon can see through said second set of superior and inferior apertures, wherein said first and said second sets of superior and inferior apertures range in cross-sectional area of from about 36 millimeters$^2$ to about 225 millimeters$^2$.

2. The invention of claim 1 further comprising a second brake attached to a second long side of said trapezoidal shaped divider, wherein said second brake extends laterally outward from said second lateral side of said trapezoidal shaped divider.

3. The invention of claim 2 further comprising a fifth support, adjacent said first and said second corner supports, wherein said fifth support is connected to said first generally trapezoidal shaped divider and extends in opposite directions from said first generally trapezoidal shaped divider.

4. The invention of claim 3 further comprising:

a) a sixth support, adjacent said first corner support and said third support, wherein said sixth support is connected to said first generally trapezoidal shaped divider and extends in opposite directions from said first generally trapezoidal shaped divider; and b) a seventh support, adjacent said second corner support and said fourth support, wherein said seventh support is connected to said first generally trapezoidal shaped divider and extends in opposite directions from said first generally trapezoidal shaped divider.

5. The invention of claim 4 further comprising one or more ties extending between said supports.

6. The invention of claim 5, wherein said first set of superior and inferior apertures are of lesser cross sectional area than said second set of superior and inferior apertures.

7. The invention of claim 6 further comprising:

a) a second generally trapezoidal shaped divider generally parallel said first generally trapezoidal shaped divider and connected with said first, second, third, forth, fifth, sixth and seventh supports extending in a first direction from said first generally trapezoidal shaped divider; and b) a third generally trapezoidal shaped divider generally parallel said first generally trapezoidal shaped divider and connected with said first, second, third, forth, fifth, sixth and seventh supports extending in a second direction from said first generally trapezoidal shaped divider.

8. The invention of claim 7, wherein said second generally trapezoidal shaped divider and said third generally trapezoidal shaped divider further comprise one or more brakes.

\* \* \* \* \*